United States Patent
Wolinsky et al.

(10) Patent No.: US 10,363,245 B2
(45) Date of Patent: Jul. 30, 2019

(54) METHODS FOR TREATING CNS LESIONS

(71) Applicant: THE BOARD OF REGENTS OF THE UNIVERSITY OF TEXAS SYSTEM, Austin, TX (US)

(72) Inventors: Jerry S. Wolinsky, Houston, TX (US); John A. Lincoln, Houston, TX (US); Leorah A. Freeman, Houston, TX (US); Ponnada A. Narayana, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/902,316

(22) Filed: Feb. 22, 2018

(65) Prior Publication Data
US 2018/0243270 A1  Aug. 30, 2018

Related U.S. Application Data

(60) Provisional application No. 62/462,130, filed on Feb. 22, 2017.

(51) Int. Cl.
*A61K 45/06* (2006.01)
*A61P 25/00* (2006.01)
*A61K 31/433* (2006.01)

(52) U.S. Cl.
CPC ............ *A61K 31/433* (2013.01); *A61K 45/06* (2013.01); *A61P 25/00* (2018.01)

(58) Field of Classification Search
None
See application file for complete search history.

(56) References Cited

U.S. PATENT DOCUMENTS

| | | |
|---|---|---|
| 3,985,892 A | 10/1976 | Roux et al. |
| 4,888,168 A | 12/1989 | Potts |
| 4,933,356 A | 6/1990 | Yablonski |
| 5,010,204 A | 4/1991 | Antonaroli et al. |
| 5,270,338 A | 12/1993 | Antonaroli et al. |
| 5,585,243 A | 12/1996 | Aster et al. |
| 5,676,849 A | 10/1997 | Sammons et al. |
| 5,716,776 A | 2/1998 | Bogart |
| 5,755,237 A | 5/1998 | Rodriguez |
| 5,789,435 A | 8/1998 | Harris et al. |
| 5,948,278 A | 9/1999 | Sammons et al. |
| 6,980,845 B1 | 12/2005 | Alsop |
| 7,369,888 B2 | 5/2008 | Alsop |
| 7,485,433 B2 | 2/2009 | Van Weeghel et al. |
| 7,540,948 B2 | 6/2009 | Collier et al. |
| 7,865,228 B2 | 1/2011 | Alsop |
| 8,143,283 B1 | 3/2012 | D'Amato |
| 8,182,663 B2 | 5/2012 | Collier et al. |
| 8,236,517 B2 | 8/2012 | Collier et al. |
| 8,483,468 B2 | 7/2013 | Shuke |
| 8,614,236 B2 | 12/2013 | Swenson |
| 9,492,495 B2 | 11/2016 | Hillmeister et al. |
| 9,511,341 B2 | 12/2016 | Lin |
| 9,611,323 B2 | 4/2017 | Dennis et al. |
| 2008/0045611 A1 | 2/2008 | Radojicic |

OTHER PUBLICATIONS

Grunwald et al., Investigative Ophthalmology & Visual Science (1992), 33(3), pp. 504-507.*
Hamasaki et al., Rinsho Shinkeigaku = Clinical Neurology (1998), 38(7), pp. 697-698 (CAS SciFinder English language abstract).*
Hamasaki et al., Rinsho Shinkeigaku = Clinical Neurology (1998), 38(7), pp. 697-699.*
Freeman, Leorah, et al. "Group and individual mapping of cortical blood flow: role in subsequent brain atrophy." *Multiple Sclerosis Journal*. 23(S1):65-66, 2017.
Grunwald, Juan E., and Harry Zinn. "The acute effect of oral acetazolamide on macular blood flow." *Investigative ophthalmology & visual science* 33.3 (1992): 504-507.
Hamasaki, S., et al. "Beneficial effects of acetazolamide on paroxysmal attacks of girdle sensation in multiple sclerosis." *Rinsho shinkeigaku= Clinical neurology* 38.7 (1998): 697-699. (English translation of abstract).
Lincoln et al., "Enhanced regional cerebral perfusion following acetazolamide: preliminary results", *Multiple Sclerosis Journal*, 23(S3):982, 2017.
Lincoln, John. "Can Improving Cerebral Perfusion Impact the Evolution of Multiple Sclerosis Lesions?." *Multiple Sclerosis Journal*, 23(S1):25, 2017.
Narayana, Ponnada A., et al. "Hypoperfusion and T1-hypointense lesions in white matter in multiple sclerosis." *Multiple Sclerosis Journal* 20.3 (2014): 365-373.
Papadaki, E. Z., et al. "Hemodynamic evidence linking cognitive deficits in clinically isolated syndrome to regional brain inflammation," *European Journal of Neurology* 21.3 (2014): 499-505.
Trapp, Bruce D., and Peter K. Styes. "Virtual hypoxia and chronic necrosis of demyelinated axons in multiple sclerosis." *The Lancet Neurology* 8.3 (2009): 280-291.

* cited by examiner

*Primary Examiner* — Brian J Davis
(74) *Attorney, Agent, or Firm* — Parker Highlander PLLC

(57) ABSTRACT

Provided herein are methods for repairing central nervous system, particularly brain, lesions in a subject comprising orally administering a carbonic anhydrase inhibitor.

18 Claims, 6 Drawing Sheets

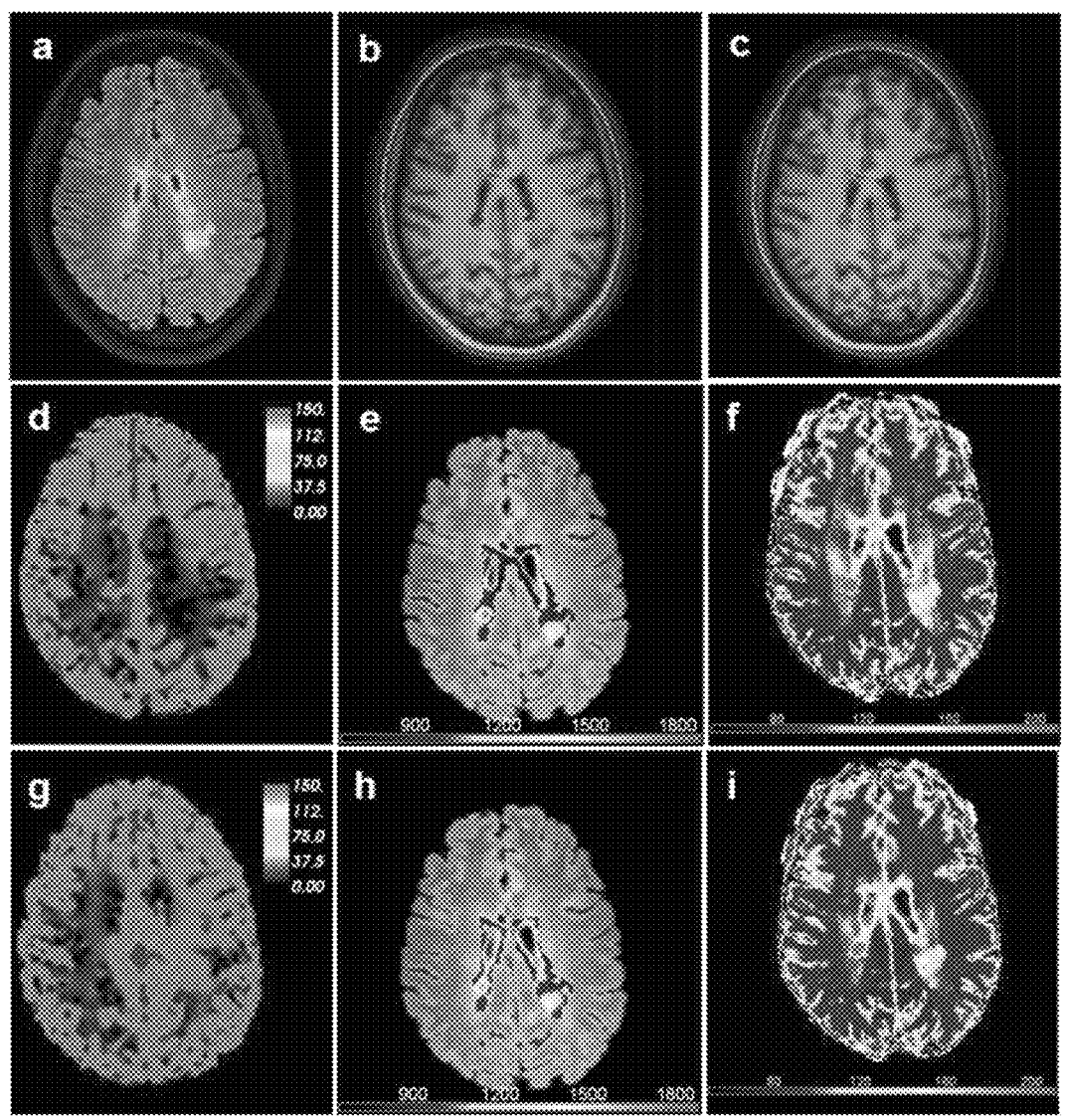
FIGS. 8a-i

METHODS FOR TREATING CNS LESIONS

This application claims the priority benefit of U.S. Provisional Patent Application No. 62/462,130, filed Feb. 22, 2017, the entire contents of which are incorporated herein by reference.

The invention was made with government support under Grant No. UL1 TR000371 awarded by the National Institutes of Health. The government has certain rights in the invention.

BACKGROUND OF THE INVENTION

1. Field of the Invention

The present invention relates generally to the field of medicine. More particularly, it concerns methods of enhancing cerebral perfusion, particularly for treating or preventing chronic neuronal lesions.

2. Description of Related Art

Alterations in cerebral perfusion occur early in multiple sclerosis (MS) (Papadaki et al., 2012; Papadaki et al., 2014; Wuerfel et al., 2004). It has been suggested that diminished regional blood flow and reduced oxygenation might deplete energy supplies in injured areas resulting in a "virtual hypoxia" thereby exacerbating neuronal degeneration (Trapp and Stys, 2009). Consistent with other published reports, previous work has shown that regions most prone to hypoperfusion are in the deep white matter which also show an increased probability of containing T1 hypointense lesions (Narayana et al., 2014).

Within T1 hypointense areas, mean diffusivity (MD), a measure of the average motion of water independent of direction, and fractional anisotropy (FA), a measure of the degree of alignment and therefore structural integrity, have been shown to correlate with the degree of tissue damage (Filippi et al., 2001). While currently approved therapies decrease the likelihood of MS lesion formation, none have been shown to impact lesions once formed. Thus, there is an unmet need for therapies to treat tissue lesions, particularly chronic lesions of the central nervous system.

SUMMARY OF THE INVENTION

In one embodiment of the present disclosure, there is provided a method of treating central nervous system (CNS) lesions in a subject comprising orally administering an effective amount of a carbonic anhydrase inhibitor to the subject. In some aspects, the amount of the carbonic anhydrase inhibitor is an effective amount to increase cerebral perfusion. In certain aspects, the subject is human. In certain aspects, the carbonic anhydrase inhibitor is acetazolamide (ACZ), dichlorphenamide, methazolamide, dorzolamide, or brinzolamide. In some specific aspects, the carbonic anhydrase inhibitor is acetazolamide (ACZ). In some aspects, the subject has been diagnosed with multiple sclerosis (MS), such as relapsing-remitting, secondary progressive, or primary progressive MS.

In certain aspects, the CNS lesion is a chronic lesion. In one aspect, the CNS lesion is an established lesion. In certain aspects, the CNS lesion is a brain lesion, such as a chronic brain lesion or a subacute brain lesion. In particular aspects, the brain lesion is a T1 hypointense lesion. In some aspects, the brain lesion is caused by cerebral hypoperfusion.

In some aspects, administering is for at least 2 months, such as for at least 6 months or at least 12 months. The administering may be once or twice daily. In some aspects, between 100 and 4000 mg of the carbonic anhydrase inhibitor is administered, such as between 200 and 4000 mg, 300 and 4000 mg, 400 and 4000 mg, 500 and 4000 mg, 1000 and 4000 mg, or 1000 and 2000 mg. In some aspects, the daily dose is split evenly. In some aspects, the dosage is 1000 mg twice daily. In some aspects, the carbonic anhydrase inhibitor is formulated for sustained release. In some aspects, the carbonic anhydrase inhibitor is formulated for immediate release.

In additional aspects, the method further comprises at least a second therapeutic. In particular aspects, the second therapeutic is a MS therapy. In some aspects, the MS therapy is administered by injection, such as subcutaneous or intramuscular injection. In some aspects, the MS therapy is glatiramer acetate, interferon beta-1β, and/or interferon-1α. In some aspects, the second therapy is anti-inflammatory. In some aspects, the MS therapy is a bone marrow or stem cell transplant. Further MS therapies that may be combined with methods of the embodiments include, but are not limited to, corticosteroids (prednisone (DELTASONE®), methylprednisolone (SOLU-MEDROL®)); ACTH (H.P. Acthar Gel); plasma exchange (plasmapheresis); beta interferons (AVONEX®, REBIF®, BETASERON®, EXTAVIA®, REBIF®, PLEGRIDY®); ocrelizumab (OCREVUS®); glatiramer acetate (COPAXONE® (glatiramer acetate injection), GLATOPA®); dimethyl fumarate (TECFIDERa®); fingolimod (GILENYA®); teriflunomide (AUBAGIO®); natalizumab (TYSABRI®); alemtuzumab (LEMTRADA®); mitoxantrone (NOVANTRONE®); physical therapy; muscle relaxants (baclofen (LIORESAL®), tizanidine (ZANAFLEX®)) medications to reduce fatigue, dizziness, tremors, depression, pain, sexual dysfunction, and bladder or bowel control problems.

In some aspects, the second therapy has no known drug-drug interactions with carbonic anhydrase inhibitors. In certain aspects, the second therapy has no known drug-drug interactions with acetazolamide.

In some embodiments, the present disclosure provides a pharmaceutical composition comprising a carbonic anhydrase inhibitor, wherein the pharmaceutical composition is formulated for oral administration. In some aspects, the carbonic anhydrase inhibitor is formulated into a tablet or capsule. In some aspects, the tablet or capsule comprises a pharmaceutically acceptable carrier. In certain aspects, the tablet or capsule comprises an enteric coating. In some aspects, the tablet or capsule comprises a single unit dosage for a human subject. In some aspects, the composition is sterile. In other aspects, the composition is not sterile. In some aspects, the composition comprises a dye or flavoring agent.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8a-i: Qualitative CBF and Tissue Integrity Measures with Oral ACZ. Qualitative CBF, DTI and T2 relaxometry measures from a selected patient (Subj 001) treated with oral ACZ at target dose (1000 mg BID) for 2 weeks. Panels a & b show T2-FLAIR and T1 images from Subj 001. Panel c shows two MS lesions that have been segmented into the T1 hypointense (red) and T2 hyperintense (blue) components (T2 rim). Panels d-f show registered qualitative pCASL, DTI and T2 relaxometry images at baseline and panels g-i show the same images after therapy with ACZ.

DESCRIPTION OF ILLUSTRATIVE EMBODIMENTS

Figure 1A:
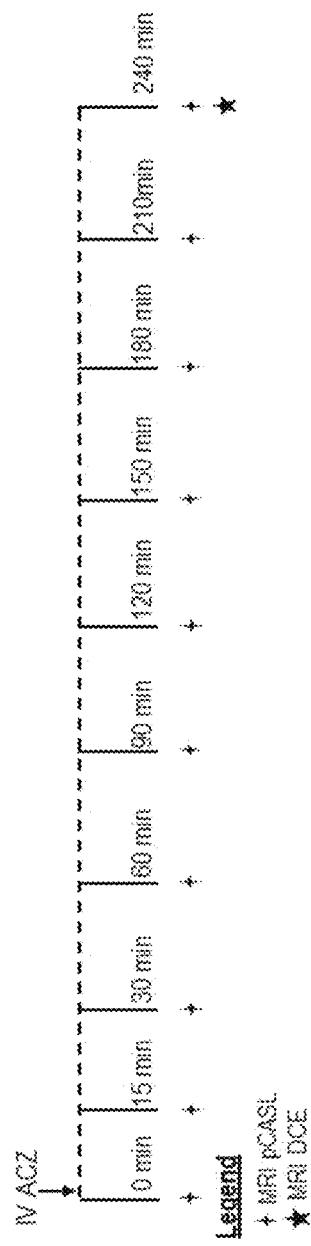
FIGS. 1A-1B: (1A) Stage 1A enrolled five patients to determine the magnitude of change in cerebral perfusion after intravenous infusion of ACZ. (1B) Stage 1B has five patients to determine the degree of change to cerebral perfusion with escalating oral ACZ administered in divided daily doses.
Figure 1B:
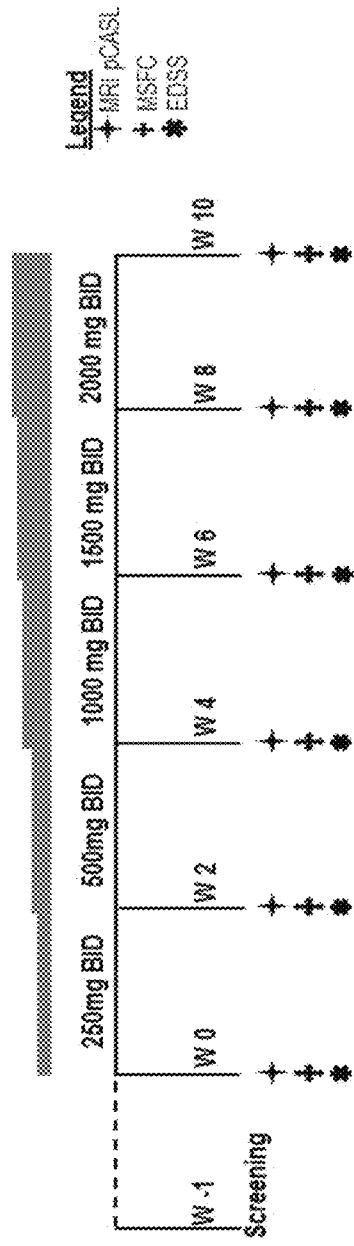
Figure 2:
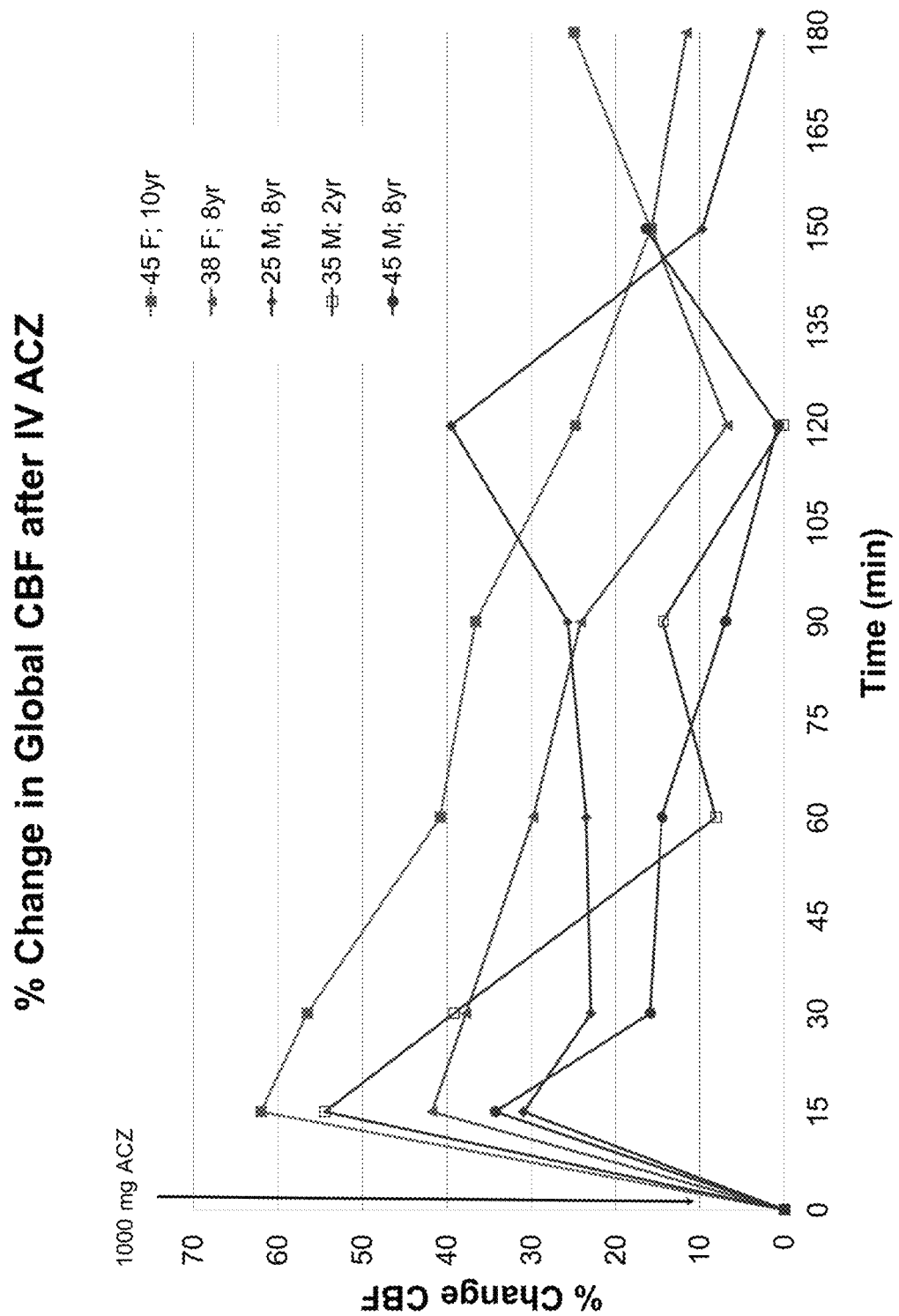
FIG. 2: Five relapsing MS subjects (age 25-45; DD 2-10 yr) were given a single 1000 mg IV ACZ bolus over three minutes. pCASL images were obtained at the indicated time intervals.

ACZ is a reversible carbonic anhydrase enzyme inhibitor. This generic medication has a good safety and tolerability profile, and is known to transiently enhance cerebral perfusion. If cerebral hypoperfusion is important in the evolution of MS lesions, then enhancing perfusion might improve tissue integrity within areas previously injured. Thus, the present studies evaluated the effect of ACZ therapy on lesion evolution in MS patients.

From the results of the clinical study, it was observed that patients had increases in global cerebral perfusion following ACZ therapy. Thus, the present disclosure provides methods for improving cerebral perfusion with oral ACZ therapy, such as over a long period of time, in order to improve tissue integrity after injury and reduce concomitant clinical disability progression.

Additional carbonic anhydrase inhibitors may be used instead of ACZ. Examples of carbonic anhydrase inhibitors include, but are not limited to, dichlorphenamide, methazolamide, dorzolamide, and brinzolamide. Dichloraphenamide has been used to treat glaucoma or occasional paralysis caused by high or low levels of potassium in the blood. Methazolamide has a longer elimination half-life than acetazolamide and is associated with fewer adverse effects to the kidneys than acetazolamide. Dorzolamide is a sulfonamide and topical carbonic anhydrase II inhibitor. Brinzolamide is a carbonic anhydrase inhibitor often used to lower intraocular pressure in patients with open-angle glaucoma

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

In the present disclosure, the term "lesion(s) of the central nervous system (CNS)" or "CNS lesion(s)" may refer to any tissue damage that may occur in the central nervous system. A CNS lesion can be, but is not limited to, a lesion in the brain, a lesion in the spinal cord, a lesion due to ischemia, a lesion due to hemorrhage, a lesion due to stroke, a lesion due to traumatic brain injury, a lesion due to spinal cord injury, a lesion due to multiple sclerosis, as well as combinations thereof. In particular aspects, the CNS lesions are lesions, such as established brain lesions, due to multiple sclerosis.

The term "treating" or "repairing" a disease or condition (e.g., injury or damage to the CNS) refers to executing a protocol, which may include administering one or more drugs to a patient, in an effort to alleviate signs or symptoms of the disease or condition. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. For example, repairing a CNS lesion may comprise promoting cerebral perfusion, revascularization and/or reenervation of a CNS lesion.

The terms "increasing," "promoting," "enhancing" refers to increasing the cerebral perfusion, neurite growth and/or neuronal regeneration in the CNS in a subject by a measurable amount using any method known in the art. The cerebral perfusion, neurite growth and/or neuronal regeneration in the CNS is increased, promoted or enhanced if the neurite growth and/or neuronal regeneration is at least about 10%, 20%, 30%>, 50%>, 80%>, or 100% increased in comparison to the cerebral perfusion, neurite growth and/or neuronal regeneration prior to administration of a carbonic anhydrase inhibitor.

The term "effective amount" as used herein refers to an amount sufficient to cause a beneficial or desired clinical result (e.g. improvement in clinical condition). A therapeutically effective amount can be administered in the form of a single dose, or a series of doses separated by intervals of days, weeks or months.

"Subject" and "patient" refer to either a human or non-human, such as primates, mammals, and vertebrates. In particular embodiments, the subject is a human.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject. In some embodiments, the dosage of antigen-specific T cell infusion may comprise about 100 million to about 30 billion cells, such as 10, 15, or 20 billion cells.

The term "EDSS" refers to an Expanded Disability Status Scale. The EDSS scale runs from 0 to 10 and is:
  0: Normal neurological examination (all grade 0 in functional systems [FS]; cerebral grade 1 acceptable)
  1: No disability, minimal signs in 1 FS (i.e. grade 1 excluding cerebral grade 1)
  1.5: No disability, minimal signs in >1 FS (>1 grade 1 excluding cerebral grade 1)
  2: Minimal disability in 1 FS (1 FS grade 2, others 0 or 1)
  2.5: Minimal disability in 2 FS (2 FS grade 2, others 0 or 1)
  3: Moderate disability in 1 FS (1 FS grade 3, others 0 or 1), or mild disability in 3-4 FS (3-4 FS grade 2, others 0 or 1) though fully ambulatory
  3.5: Fully ambulatory but with moderate disability in 1 FS (1 FS grade 3) and 1-2 FS grade 2; or 2 FS grade 3; or 5 FS grade 2 (others 0 or 1)
  4: Fully ambulatory without aid, self-sufficient, up and about some 12 hours a day despite relatively severe disability consisting of 1 FS grade 4 (others 0 or 1), or combinations of lesser grades exceeding limits of previous steps. Able to walk without aid or rest some 500 m
  4.5: Fully ambulatory without aid, up and about much of the day, able to work a full day, may otherwise have some limitation of full activity or require minimal assistance; characterized by relatively severe disability, usually consisting of 1 FS grade 4 (others 0 or 1) or combinations of lesser grades exceeding limits of previous steps. Able to walk without aid or rest for some 300 m
  5: Ambulatory without aid or rest for about 200 m; disability severe enough to impair full daily activities (e.g., to work full day without special provisions). (Usual FS equivalents are 1 grade 5 alone, others 0 or 1; or combination of lesser grades usually exceeding specifications for step 4.0)
  5.5: Ambulatory without aid or rest for about 100 m, disability severe enough to preclude full daily activities. (Usual FS equivalents are 1 grade 5 alone, others 0 or 1; or combination of lesser grades usually exceeding those for step 4.0)

6: Intermittent or unilateral constant assistance (cane, crutch or brace) required to walk about 100 m with or without resting. (Usual FS equivalents are combinations with >2 FS grade 3+)

6.5: Constant bilateral assistance (canes, crutches or braces) required to walk about 20 m without resting. (Usual FS equivalents are combinations with >2 FS grade 3+)

7: Unable to walk beyond about 5 m even with aid, essentially restricted to wheelchair; wheels self in standard wheelchair and transfers alone; up and about in wheelchair some 12 hours a day. (Usual FS equivalents are combinations with >1 FS grade 4+; very rarely, pyramidal grade 5 alone)

7.5: Unable to take more than a few steps; restricted to wheelchair, may need aid in transfer; wheels self but cannot carry on in standard wheelchair a full day; may require motorized wheelchair. (Usual FS equivalents are combinations with >1 FS grade 4+)

8: Essentially restricted to bed or chair or perambulated in wheelchair, but may be out of bed itself much of the day; retains many self-care functions; generally has effective use of arms. (Usual FS equivalents are combinations, generally 4+ in several systems)

8.5: Essentially restricted to bed much of the day; has some effective use of arm(s); retains some self-care functions. (Usual FS equivalents are combinations, generally 4+ in several systems)

9: Helpless bedridden patient; can communicate and eat. (Usual FS equivalents are combinations, mostly grade 4+)

9.5: Totally helpless bedridden patient; unable to communicate effectively or eat/swallow. (Usual FS equivalents are combinations, almost all grade 4+)

10: Death due to multiple sclerosis

II. TREATMENT OF TISSUE DAMAGE

Certain embodiments of the present disclosure concern compositions comprising a carbonic anhydrase inhibitor for the prevention and/or treatment of tissue damage, such as lesions in the central nervous system. In particular embodiments, the tissue damage is in an established or chronic lesion which may be due to diminished blood flow and/or reduced oxygenation. The lesions may be in the brain, such as in the deep white matter. For example, a subject with multiple sclerosis may have hypoperfusion in certain areas of the brain which results in the evolution of lesion formation. The present methods comprising administering a carbonic anhydrase inhibitor may involve enhancing cerebral perfusion to improve tissue integrity and/or reduce concomitant clinical disability progression.

In various embodiments, the subject has experienced an injury, particularly tissue damage, to the central nervous system. For example, the subject may have a neurodegenerative disease. In some embodiments, has experienced a surgical resection, spinal cord injury or a traumatic brain injury. In some embodiments, the central nervous system disease, disorder or injury is selected from the group consisting of cranial or cerebral trauma, spinal cord injury, CNS injury resulting from tumor resection, transverse myelitis, optical myelitis, Guillain-Barre syndrome (GBS), stroke, multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Merzbacher disease, Spongy degeneration, Alexander's disease, Canavan's disease, metachromatic leukodystrophy, and Krabbe's disease. In particular embodiments, the subject has multiple sclerosis.

An inhibitor of the enzyme carbonic anhydrase is a compound that, when in the presence of the enzyme and substrate for the enzyme, is capable of reducing the activity of the enzyme compared to the same circumstances of the enzyme when the compound is not present. It is well known to the skilled person to ascertain whether or not a compound is an inhibitor of carbonic anhydrase, using standard enzyme kinetic measurements and using known assays developed for carbonic anhydrase. Suitable assays are described, for example, in Dodgson et al., *J Appl Physiol*, 68:2443-2450, 1990.

Exemplary carbonic anhydrase inhibitors that may be used in the present methods include, but are not limited to, acetazolamide (ACZ), dichlorphenamide, methazolamide (a compound with longer elimination half-life than acetazolamide and that is less associated with adverse effects to the kidney sold as e.g., Neptazane), dorzolamide (a carbonic anhydrase II inhibitor sold as e.g., TRUSOPT®, DARANIDE® OR KEVEYIS®), brinzolamide (also known as AZOPT® and BEFARDIN®) and certain thiophene sulfonamides. Generally, the skilled person will be aware that certain types of sulfonamides and sulfamates can be suitable inhibitors of carbonic anhydrase, in particular heteroaromatic nitrogen containing sulfonamides and sulfamates. Other effective carbonic anhydrase inhibitors are reported in, for example, U.S. Pat. Nos. 4,383,098, 4,416,890, 4,426388, 4,677,115, 4,797,413, 4,820,848, 4,824,968, 4,863,922, 5,157,044, and 5,225424, which all are incorporated herein by reference.

In one embodiment, the composition is for oral administration. In case of a composition for oral treatment, acetazolamide, dichlorphenamide and methazolamide are suitable to be used as carbonic anhydrase inhibitors. In particular embodiments, the carbonic anhydrase inhibitor is ACZ. For example, the ACZ can be administered as a 250 mg prolonged-release capsule (e.g., DIAMOX SR®). In further examples, the ACZ can be administered as a 500 mg prolonged-release capsule.

The composition may be administered daily, such as once or twice daily. The composition may be administered over a long period of time, such as at least 1 month. For example, the composition can be administered over 2, 3, 4, 5, 6, or more months. The time period for which the subject is dosed with the carbonic anhydrase inhibitor in any of the present methods can range, for example, from about 1 week to the remaining lifespan of the subject. The carbonic anhydrase inhibitor and its composition can be dosed, for example, at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 20 weeks, at least 30 weeks, at least 40 weeks, at least 50 weeks, at least 1 year, at least 60 weeks, at least 70 weeks, at least 80 weeks, at least 90 weeks, at least 100 weeks, at least 2 years, at least 3 years, at least 4 years, at least 5 years, at least 6 years, at least 7 years, at least 8 years, at least 9 years, at least 10 years, at least 20 years, at least 30 years, at least 40 years, at least 50 years, at least 60 years, at least 70 years, at least 80 years, at least 90 years, or at least 100 years.

In one embodiment, the carbonic anhydrase inhibitor and its composition can be dosed, for example, for a period of time ranging from about 1 week to about 100 years, about 1 week to about 90 years, about 1 week to about 80 years, about 1 week to about 70 years, about 1 week to about 60 years, about 1 week to about 50 years, about 1 week to about 40 years, about 1 week to about 30 years, about 1 week to about 20 years, about 1 week to about 10 years, about 1 week to about 9 years, about 1 week to about 8 years, about 1 week to about 7 years, about 1 week to about 6 years, about 1 week to about 5 years, about 1 week to about 4 years, about 1 week to about 3 years, about 1 week to about 2 years, about 1 week to about 100 weeks, about 1 week to about 1 year, about 1 week to about 50 weeks, about 1 week to about 40 weeks, about 1 week to about 30 weeks, about 1 week to about 20 weeks, about 1 week to about 10 weeks, or about 1 week to about 5 weeks. In another embodiment, the carbonic anhydrase inhibitor and its composition can be dosed, for example, about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 1 year, about 60 weeks, about 70 weeks, about 80 weeks, about 90 weeks, about 100 weeks, about 2 years, about 3 years, about 4 years, about 5 years, about 6 years, about 7 years, about 8 years, about 9 years, about 10 years, about 20 years, about 30 years, about 40 years, about 50 years, about 60 years, about 70 years, about 80 years, about 90 years, or about 100 years.

A. Multiple Sclerosis Lesions

In particular embodiments, the lesions treated, repaired, and/or prevented by the present methods and compositions are due to multiple sclerosis. Accordingly, the carbonic anhydrase inhibitor may be used to treat lesions (e.g., chronic lesions), reduce the number of lesions, or prevent the formation of new lesions in a subject with MS. The lesions may be T2 lesions, T1 hypointense lesions, and/or Gd+ lesions. In particular aspects, the lesions are T1 hypointense lesions. The reduction in lesions can be ascertained by routine magnetic resonance imaging ("MRI") methods.

There are four major clinical types of MS: 1) relapsing-remitting MS ("RR-MS"), characterized by clearly defined relapses with full recovery or with sequelae and residual deficit upon recovery; periods between disease relapses characterized by a lack of disease progression; 2) secondary progressive MS ("SP-MS"), characterized by initial relapsing remitting course followed by progression with or without occasional relapses, minor remissions, and plateaus; 3) primary progressive MS ("PP-MS"), characterized by disease progression from onset with occasional plateaus and temporary minor improvements allowed; and 4) progressive relapsing MS ("PR-MS"), characterized by progressive disease onset, with clear acute relapses, with or without full recovery; periods between relapses characterized by continuing progression.

The pathology of MS is characterized by an abnormal immune response directed against the central nervous system. In particular, T-lymphocytes are activated against the myelin sheath of the central nervous system causing demyelination. In the demyelination process, myelin is destroyed and replaced by scars of hardened "sclerotic" tissue which is known as plaque. These lesions appear in scattered locations throughout the brain, optic nerve, and spinal cord. Demyelination interferes with conduction of nerve impulses, which produces the symptoms of multiple sclerosis. Most patients recover clinically from individual bouts of demyelination, producing the classic remitting and exacerbating course of the most common form of the disease known as relapsing-remitting multiple sclerosis.

MS pathology is, in part, reflected by the formation of focal inflammatory demyelinating lesions in the white matter, which are the hallmarks in patients with acute and relapsing disease. Initial formation of lesions is often associated with acute perivenular inflammation and blood brain barrier disruption demonstrable by tissue enhancement demonstrated on magnetic resonance imaging (MRI) following the intravenous administration of gadolinium containing contrast agents. In patients with progressive disease, the brain is affected in a more global sense, with diffuse but widespread (mainly axonal) damage in the normal appearing white matter and demyelination also in the grey matter, particularly, in the cortex.

Patients having multiple sclerosis may be identified by criteria establishing a diagnosis of clinically definite multiple sclerosis. Briefly, an individual with clinically definite multiple sclerosis has had two attacks and clinical evidence of either two lesions or clinical evidence of one lesion and paraclinical evidence of another separate lesion. Definite multiple sclerosis may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose multiple sclerosis. The McDonald criteria include the use of Mill evidence of CNS impairment over time to be used in diagnosis of multiple sclerosis, in the absence of multiple clinical attacks.

Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a means to grade clinical impairment due to multiple sclerosis. Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to multiple sclerosis). A decrease of one full step indicates an effective treatment.

Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images. MRI can be used to measure active lesions using gadolinium-DTPA-enhanced imaging or the location and extent of lesions using T2-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of multiple sclerosis lesions can be determined by radiologists. Areas of lesions can be outlined and summed slice by slice for total lesion area. Three analyses may be done: evidence of new lesions, rate of appearance of active lesions, percentage change in lesion area. Improvement due to therapy can be established by a statistically significant improvement in an individual patient compared to baseline or in a treated group versus a placebo group.

In one embodiment of the present methods, administration of the carbonic anhydrase inhibitor or composition containing the carbonic anhydrase inhibitor to a subject or group of subjects results in reducing the frequency of relapse in the subject relative to subject or group of subjects treated with placebo. "Reduction in the frequency of relapse" means that the number of relapses in a treated subject or a group of treated subjects are decreased relative to the number of relapses in a subject or a group of subjects treated with placebo. For example, a 50% reduction in frequency of relapse means that the group of treated subjects had on average 50% fewer relapses than the placebo group.

Disability progression may be measured by EDSS. The risk of disability progression in any subject or group of subjects treated by the present methods can be reduced by, for example: about 20% to about 40%, such as about 30% to about 40%.

B. Pharmaceutical Compositions

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

The pharmaceutical dosage units of the present disclosure may be formulated for various forms of administration, including, for example, sublingual, mucosal, parenteral, intravenous, intramuscular, buccal, lingual, intra-lingual, nasal, intra-sinus, intraocular, topical, oral, vaginal, urethral, subcutaneous, peritoneal, intra-arterial, and by inhalation and/or transdermal administration and combinations thereof. In particular embodiments, the composition is formulated for oral delivery. Consistent with the various forms of administration, the pharmaceutical dosage unit can generally be formulated, for example, as a tablet, capsule, injection, and/or patch.

Sublingual tablets are designed to dissolve very rapidly. Examples of such formulations include ergotamine tartrate, isosorbide dinitrate, isoproterenol HCl. The necessary ingredients for the pharmaceutical dosage unit may be processed in accordance with known methods, using or incorporating familiar coatings and additives as required. By way of example only, in addition to the pharmaceutically active components, a dosage unit may contain effective amounts of binders, fillers, disintegrants, sustained-release agents, diluents, anti-adherents, glidants, flow aids, plasticizers and lubricants, which are well known in the field of pharmaceutical processing. For instance, the formulation of these tablets may contain, in addition to the active agent, a limited number of soluble excipients, including a binder such as povidone or hydroxypropyl methylcellulose (HPMC), diluents such as lactose, mannitol, starch or cellulose, a disintegrant such as pregelatinized or modified starch, lubricants such as magnesium stearate, stearic acid or hydrogenated vegetable oil, a sweetener such as saccharin or sucrose and suitable flavoring and coloring agents. The process of making sublingual tablets generally involves moistening the blended powder components with an alcohol-water solvent system containing approximately 60% alcohol and 40% water and pressing this mixture into tablets.

The pharmaceutical dosage unit may be presented in a single dose or as divided doses administered at appropriate intervals, for example, as two, three, four or more sub-doses per day. In one embodiment, the pharmaceutical dosage unit may be formulated such that a single sublingual tablet is administered twice daily.

Alternatively, the pharmaceutical dosage unit may be formulated so that the active ingredient exhibits sustained-release characteristics upon administration to the patient. For example, the active ingredient may be delivered with an oral mucosal patch. Methods of making such patches are well known to one of skill in the art. In one embodiment, the oral mucosal patch is prepared by homogeneously mixing the active component with appropriate amounts of Carbopol 934, polyisobutylene, and polyisoprene using a two-roll mill and then compressing the mixture to the appropriate thickness. A membrane backing such as ethylcellulose is then applied to one side of the compressed material and circular disks, having an area of about 0.5 cm$^2$ and thickness of about 0.6 mm for example, may be punched from the material. The backing inhibits drug release from one side of the disk and reduces adhesion to opposing side tissues. The oral mucosal patches may be secured to mucosal buccal surfaces such as the gums, lips, and cheeks, and worn for extended periods. In one instance, the oral mucosal patches may be work for about 12 hours.

In another sustained release embodiment, the active ingredient may be delivered using a tablet-form dosage unit having a partially hydrophilic matrix which exhibits sustained release of the active component. In addition to the active ingredient, the tablet is comprised of, for example, ethylcellulose as a sustained-release agent and hydroxypropyl methylcellulose (HPMC) as a film former. Further, bulking agents such as microcrystalline cellulose and starch, a polyvinylpyrrolidone binder, silicon dioxide as an anti-adherent, dibutyl sebacate as a plasticizer, and magnesium stearate as a lubricant may be included. Using conventional processes, the listed ingredients, other than ethylcellulose, HPMC and dibutyl sebacate, are combined and pressed into a tablet. The tablet is then coated with the ethylcellulose, HPMC and dibutyl sebacate prior to administration of the tablet. When this tablet encounters an aqueous environment, such as the mucosal buccal surfaces, portions of the tablet coating dissolve, leaving a non-continuous film of water-insoluble ethylcellulose surrounding the remaining tablet core. The rate of diffusion of the active ingredients from the tablet core into the aqueous environment is determined by the concentration of ethylcellulose, HPMC and dibutyl sebacate in the coating.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment of the present disclosure, the compound is given in a dosage lying in a range of from about 1 to about 1000 mg, such as for example about 1 to 500 mg, 5 to 500 mg, 5 to 250 mg, 10 to 200 mg or 1 to about 4000 mg, such as for example about 1 to 1500 mg, 5 to 1500 mg, 5 to 1250 mg, 10 to 2000 mg, 10 to 2500 mg, 15 to 3000 mg, 15 to 3500 mg, or 20 to 4000 mg. The patient may be administered a dosage whenever the patient experiences pain. Hence, the dosage may be administered 1, 2, 3, 4, 5, 6, 7, 8, 9 or 10 times during a 24 hour period. The physician will in any event determine the actual dosage, which will be most suitable for any particular patient and it may vary with the severity of disease, age, weight and response of the particular patient. The above dosages are, of course only exemplary of the average case and there may be instances where higher or lower doses are merited and such are within the scope of the invention.

Another way of expressing the dosage level in accordance with the present disclosure is as mg/kg bodyweight. Accordingly, for administration to human patients the dosage levels of the compounds in accordance with the present disclosure, or pharmaceutically acceptable salts, solvates, or prodrugs thereof, will be in a range from about 0.01 to about 15 mg/kg bodyweight, such as for example from about 0.01 to about 10 mg/kg bodyweight, about 0.05 to about 10 mg/kg bodyweight, 0.05 to 5 mg/kg bodyweight or 0.1 to 2.5 mg/kg bodyweight.

In yet another way of expressing the dosage is as unit dosages. Such unit dosages may be administered one or more time during the day and is typically administered whenever the patient feels the need to be treated. In some embodiments the unit dosage of the compounds in accordance with the present invention will be in a range of from about 0.01 to about 0.2 mg/kg bodyweight, such as for example from about 0.01 to 0.10 mg/kg bodyweight, about 0.02 to 0.08 mg/kg bodyweight, about 0.03 to 0.07 mg/kg bodyweight or 0.04 to 0.06 mg/kg bodyweight. In another embodiment the dosage is 0.05 mg/kg bodyweight. The compounds for use in accordance with the present invention may be administered alone, or as part of a combination therapy. If a combination of active agents is administered, then it may be administered simultaneously, separately or sequentially. Depending on the disease and the state of the disease to be treated, it may be relevant to include one or more additional active compound in the medicament.

In various embodiments, the pharmaceutical compositions may have a drug loading, such that the active component comprises about 0.5-90 weight percent of the pharmaceutical composition, 1-50 weight percent of the pharmaceutical composition, 1-25 weight percent of the pharmaceutical composition, or 1-10 weight percent of the pharmaceutical composition. In various embodiments, the amount of active component is present in the pharmaceutical composition in a range from about 0.1% to about 40% by weight (including 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.5-5%, 5-10% and 10-20%, etc.).

In various embodiments, the pharmaceutical composition may comprise 0.1 µg, 0.2 µg, 0.3 µg, 0.4 µg, 0.5 µg, 0.6 µg, 0.7 µg, 0.8 µg, 0.9 µg, 1 µg, 10 µg, 20 µg, 30 µg, 40 µg, 50 µg, 60 µg, 70 µg, 80 µg, 90 µg, 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 350 mg, 400 mg, 450 mg, 500 mg, 550 mg, 600 mg, 650 mg, 700 mg, 750 mg, 800 mg, 850 mg, 900 mg, 950 mg; 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, or 4000 mg of active component.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration three times a day, twice a day, every day, every two days, every three days, every four days, every five days, every six days, a weekly basis, a monthly basis or any set number of days or weeks there-between.

For oral administration to human patients, the daily dosage level of the carbonic anhydrase inhibitor such as ACZ, their pharmaceutically acceptable salts, and pharmaceutically acceptable solvates of either entity, when used in accordance with the invention. In other embodiments for oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

In still other embodiments, such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavoring agents, coloring matter or dyes, with emulsifying and/or suspending agents and with diluents such as water, ethanol, propylene glycol and glycerin, and combinations thereof.

In some embodiments, modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form i.e. upon the surface or coating.

In certain preferred embodiments, a composition of the embodiments is administered orally and is formulated to facilitate such oral administration. Thus, in some embodiments a composition may comprise, for example, solutions, suspensions, emulsions, tablets, pills, capsules (e.g., hard or soft shelled gelatin capsules), sustained release formulations, buccal compositions, troches, elixirs, suspensions, syrups, or combinations thereof. Oral compositions may be incorporated directly with a food or drink product (e.g., along with a fruit juice or alcohol). Preferred carriers for oral administration comprise inert diluents, assimilable edible carriers or combinations thereof. In other aspects, the oral composition may be prepared as a syrup or elixir. A syrup or elixir, and may comprise, for example, at least one active agent, a sweetening agent, a preservative, a flavoring agent, a dye, a preservative, or combinations thereof.

In further aspects, a composition comprising a carbonic anhydrase inhibitor can be formulated into a capsule or tablet for oral administration. In some aspects, the capsule is substantially impermeable to gas, and preferably the capsule is formulated to dissolve in the gastrointestinal tract of a subject.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

A composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can comprise a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

C. Combination Therapy

In another embodiment of the present disclosure, the method for repairing, treating, or preventing a CNS lesion, such as a multiple sclerosis lesion, in a subject in need thereof comprises the administration to said subject of an effective amount of the carbonic anhydrase inhibitor in combination with one or more therapeutic agents. The therapies could be provided in a combined amount effective to repair CNS lesions in a subject. This process may involve contacting the patient with the agents/therapies at the same time. This may be achieved by contacting the patient with a single composition or pharmacological formulation that includes both agents, or by administering two distinct compositions or formulations, at the same time, wherein one composition includes the carbonic anhydrase inhibitor.

Alternatively, the treatment according to the present disclosure may precede or follow the other treatment by intervals ranging from minutes to weeks. In embodiments where the standard treatment and the carbonic anhydrase inhibitor are administered separately, one would generally ensure that a significant period of time did not expire between the times of each delivery, such that the therapies would still be able to exert an advantageously combined effect on the cell. In such instances, it is contemplated that one would administer both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

In particular aspects, the one or more therapeutic agents are used for treating multiple sclerosis. Examples of therapeutic agents commonly used for treating multiple sclerosis that may be used in combination with a carbonic anhydrase inhibitor include, but are not limited to interferons (e.g., human interferon beta-1α (e.g., AVONEX®, REBIF®, PLEGRIDY®) and interferon beta-Ib (BETASERON™, EXTAVIA®); human interferon beta substituted at position 17; Berlex/Chiron), glatiramer acetate (also termed Copolymer 1, Cop-1; COPAXONE™; Teva Pharmaceutical Industries, Inc.) and derivatives, fumarates (e.g., dimethyl fumarate (e.g., FUMADERM®, TECFIDERA®)), RITUXAN® (rituximab) or another anti-CD20 antibody (e.g., one that competes with or binds an overlapping epitope with rituximab), mitoxantrone (NOVANTRONE®, Lederle), a chemotherapeutic (e.g., clabribine (LEUSTATIN®), azathioprine (IMURAN®), cyclophosphamide (CYTOXAN®), cyclosporine-A, methotrexate, 4-aminopyridine, and tizanidine, a corticosteroid (e.g., methylprednisolone (MEDRONE®, Pfizer), prednisone), an immunoglobulin (e.g., RITUXAN® (rituximab); CTLA4 Ig; alemtuzumab (LEMTRADA®, MABCAMPATH®) or daclizumab (an antibody that binds CD25); ocrelizumab (OCREVUS®)), statins, immunoglobulin G intravenous (IgGIV), Natalizumab (TYSABRI®) anti-integrin alpha-4 antibody, the oral CC chemokine receptor 1 antagonist BX471 (ZK811752), FTY720 (fingolimod (GILENYA®)), teroflunomide (AUBAGIO®), antibodies or antagonists of human cytokines or growth factors (e.g., TNF, LT, IL-1, IL-2, IL-6, IL-7, IL-8, IL-12, IL-15, IL-16, IL-17, IL-18, IL-23, EMAP-I1, GM-CSF, FGF, and PDGF), antibodies to cell surface molecules (e.g., CD2, CD3, CD4, CD8, CD25, CD28, CD30, CD40, CD45, CD69, CD80, CD86, CD90 or their ligands), FK506, rapamycin, mycophenolate mofetil, leflunomide, non-steroidal anti-inflammatory drugs (NSAIDs) (e.g., phosphodiesterase inhibitors, adenosine agonists, antithrombotic agents, complement inhibitors, adrenergic agents, agents that interfere with signaling by proinflammatory cytokines as described herein, IL-I[beta] converting enzyme inhibitors (e.g., Vx740), anti-P7s, PSGL, TACE inhibitors, T-cell signaling inhibitors (e.g., kinase inhibitors, metal loproteinase inhibitors, sulfasalazine, azathloprine, 6-mercaptopurines, angiotensin converting enzyme inhibitors), corticosteroids (e.g., prednisone, methylprednisolone), ACTH, plasma exchange (plasmapheresis), amantadine, baclofen, papaverine, meclizine, hydroxyzine, sulfamethoxazole, ciprofloxacin, docusate, pemoline, dantrolene, desmopressin, dexamethasone, tolterodine, phenyloin, oxybutynin, bisacodyl, venlafaxine, amitriptyline, methenamine, clonazepam, isoniazid, vardenafil, nitrofurantoin, psyllium hydrophilic mucilloid, alprostadil, gab apentin, nortriptyline, paroxetine, propantheline bromide, modafinil, fluoxetine, phenazopyridine, methylprednisolone, carbamazepine, imipramine, diazepam, sildenafil, bupropion, and sertraline. ACZ may be used in conjunction with physical therapy. ACZ may further be used in conjunction with medications to reduce fatigue, dizziness, tremors, depression, pain, sexual dysfunction, and bladder or bowel control problems. Examples of combination therapies currently used include glatiramer acetate and albuterol; glatiramer acetate and minocycline; interferon-beta 1a and mycophenolate mofetil; and BHT-3009 and atorvastatin.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Clinical Study on Improving Cerebral Perfusion with ACZ for the Treatment of MS Lesions A novel staged proof-of-concept, prospective, randomized, placebo-controlled, delayed start clinical trial was designed that utilizes adjunct daily oral therapy with ACZ to durably improve cerebral perfusion in MS patients to determine the degree to which improved perfusion impacts lesion evolution.

The primary objective is to assess absolute and relative change in regional cerebral perfusion using pseudo-continuous arterial spin labeling (pCASL) and dynamic susceptibility contrast techniques and relate to quantitative measures of diffusivity and volumes within discrete MS lesions.

Secondary objectives include determining the degree of change in mean diffusivity within MS lesions in regions with increased cerebral perfusion compared with areas not as well perfused. In addition, composite changes in disability measures after ACZ compared to baseline are determined. Disability measures include 9-hole peg test time for either dominant or non-dominant hand, timed 25-foot walk and symbol digit modality test. Composite change of at least 20% in any of the disability measures is evaluated. The changes in the patient-reported outcome measures Modified Fatigue Impact Scale (MFIS), Twelve Item MS Walking Scale (MSWS-12) and the 36-Item Short Form Survey (SF-36) are also determined.

Inclusion criteria include age between 18 and 55 years, inclusive; diagnosis of relapsing forms of MS using revised McDonald criteria (Polman et al., 2011); stable on either subcutaneous glatiramer acetate (COPAXONE®), or interferon beta-1β (BETASERON®, EXTAVIA®), or interferon beta-1α (REBIF®), or intramuscular interferon beta-1α (AVONEX®); EDSS 0-6.0 inclusive; and ability to understand and sign written informed consent, obtained prior to undergoing any study-related procedure, including screening tests. The term "stable" implies that the subject has not had change in therapy for any reason for the 6 months prior to study entry.

The exclusion criteria include known hypersensitivity to sulfonamides or derivatives; known history of renal or hepatic disease, cardiovascular disease including stroke, transient ischemic attack, myocardial infarction, angina or congestive heart failure; evidence of hyponatremia or hypokalemia, marked kidney dysfunction defined as creatinine greater than 2.0 mg/dL, liver disease dysfunction defined as aspartate aminotransferase (AST) or alanine aminotransferase (ALT) greater than three-fold upper limit of normal (ULN); initiation of new immunosuppressant treatment after the subject becomes protocol-eligible (except for corticosteroids) or enrolment in a concurrent trial; any history of cytopenia; history of pulmonary obstruction or emphysema; positive pregnancy test, inability or unwillingness to use effective means of birth control; and presence of metallic objects implanted in the body that would preclude the ability of the subject to safely have MRI exams.

The subjects were assessed by MRI scans. The scanner is the 3-Telsa Philips Ingenia scanner using an eight channel SENSE-compatible head coil (Philips Medical Systems, Best, Netherlands), 3D-MPRAGE, and pCASL (LD=1900 ms; PLD=2000 ms; 70 dynamics).

Surface reconstruction and volumetric segmentation were obtained from the 3D-MPRAGE volumes with the Freesurfer v5.3.0 image analysis suite (found on the internet at: surfer.nmr.mgh.harvard.edu/). pCASL images were processed using BASIL, part of the FMRIB Software Library v5.0.7 (found on the internet at: fsl.fmrib.ox.ac.uk/fsl). Cerebral blood flow (CBF) maps were registered to 3D-MPRAGE images using a boundary-based registration method.

Stage 1A of the clinical study determined that a single bolus of IV ACZ was generally well tolerated without serious AEs in the small cohort of five MS patients. Rapid increases in global cerebral perfusion following IV ACZ were measured using pCASL. In healthy controls, cerebral blood flow (CBF) has been reported to return near baseline within 60 minutes in healthy controls. Unlike historical reports, global CBF in the current patients returned near baseline in 120 minutes. Thus, adjunct therapies such as ACZ over a long period of time might improve tissue integrity after injury and reduce concomitant clinical disability progression.

Example 2—Clinical Study on the Oral Efficacy of ACZ for Improving Cerebral Perfusion in the Treatment of MS Lesions IV Administration Preliminary Results—

Figure 3:
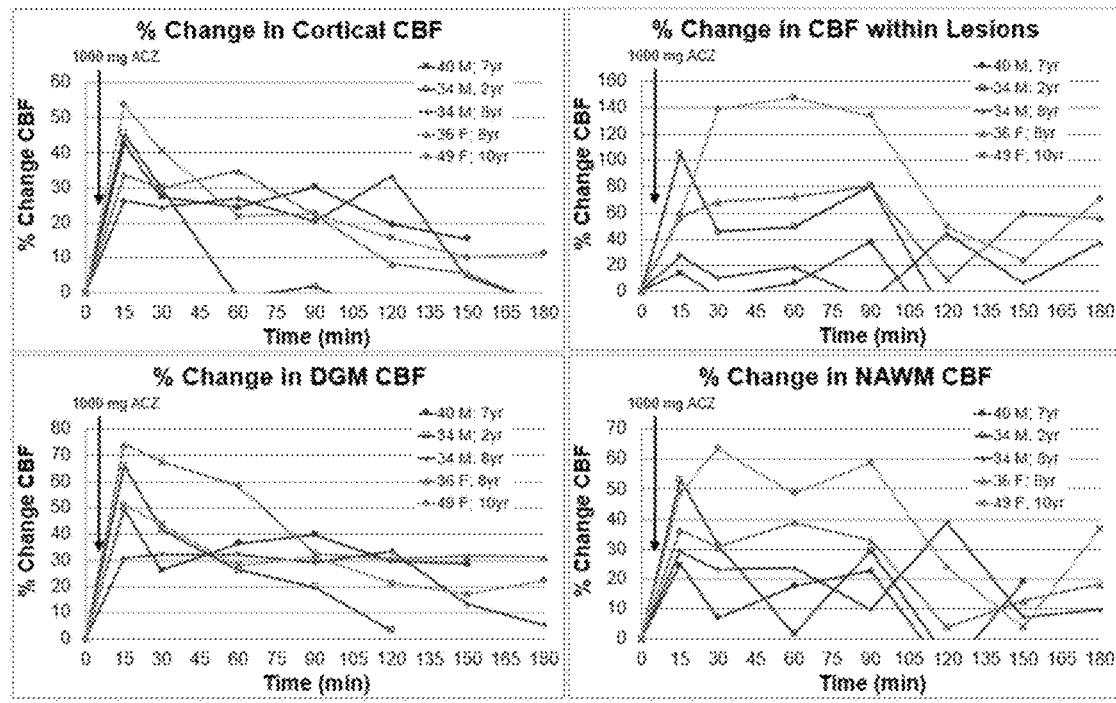
FIG. 3: Change in Global CBF After IV ACZ Infusion. Five relapsing MS patients (Age 34-49; disease duration 2-10 years) were given a single 1000 mg IV ACZ bolus over three minutes. pCASL images were obtained at the indicated time intervals and % change in CBF was calculated for cortical CBF, CBF within lesions, deep grey matter (DGM), and normal appearing white matter (NAWM).
Figure 4:
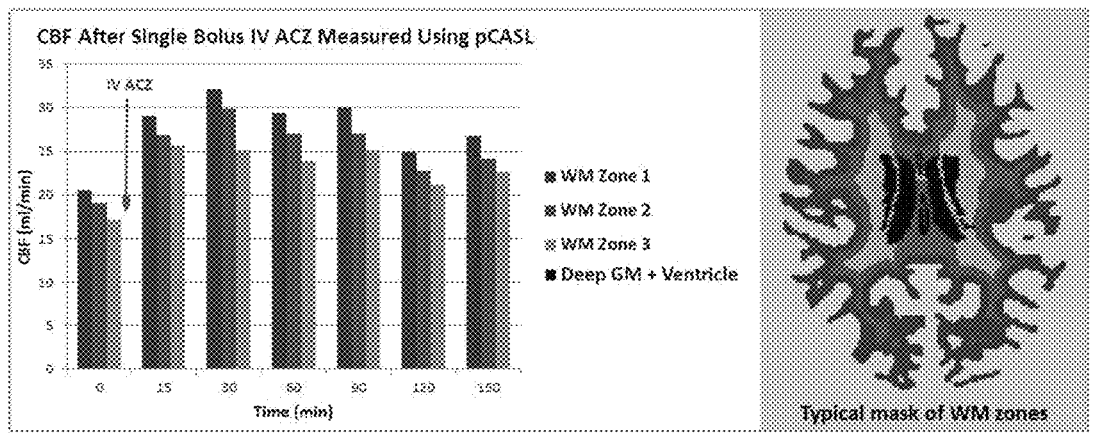
FIG. 4: pCASL Measurement of Absolute CBF in White Matter (WM) Zones. Absolute CBF in ml/100 cc/min for a representative patient are shown at baseline and at various time points after 1000 mg bolus of ACZ infused over 3 minutes. Masks of WM zones are individualized and generated using FreeSurfer v 5.3.0 by eroding segmented whole WM by a fixed percent.

All MRI studies discussed as preliminary or proposed investigations are performed on a dedicated 3.0 T Philips Ingenia research scanner with maximum gradient amplitude of 40 mT/m and a 15-channel SENSE-compatible head coil (Philips Medical Systems, Best, Netherlands) housed in the Image Analysis laboratory within the McGovern Medical School. Using pCASL measures, it was determined that from 30% to 60% peak increases in global CBF in five MS patients following a single 1000 mg IV bolus of ACZ. Increases in CBF above baseline were sustained for up to 180 minutes, regardless of region (FIG. 3). The duration of sustained increased perfusion in the patients with MS is longer than that previously described in healthy controls. Similar differences were seen when evaluating absolute CBF in regions of white matter (WM) from subcortical WM to periventricular WM zones (WM Zones 1-3) (FIG. 4).

Oral Administration Preliminary Results—

Figure 5:
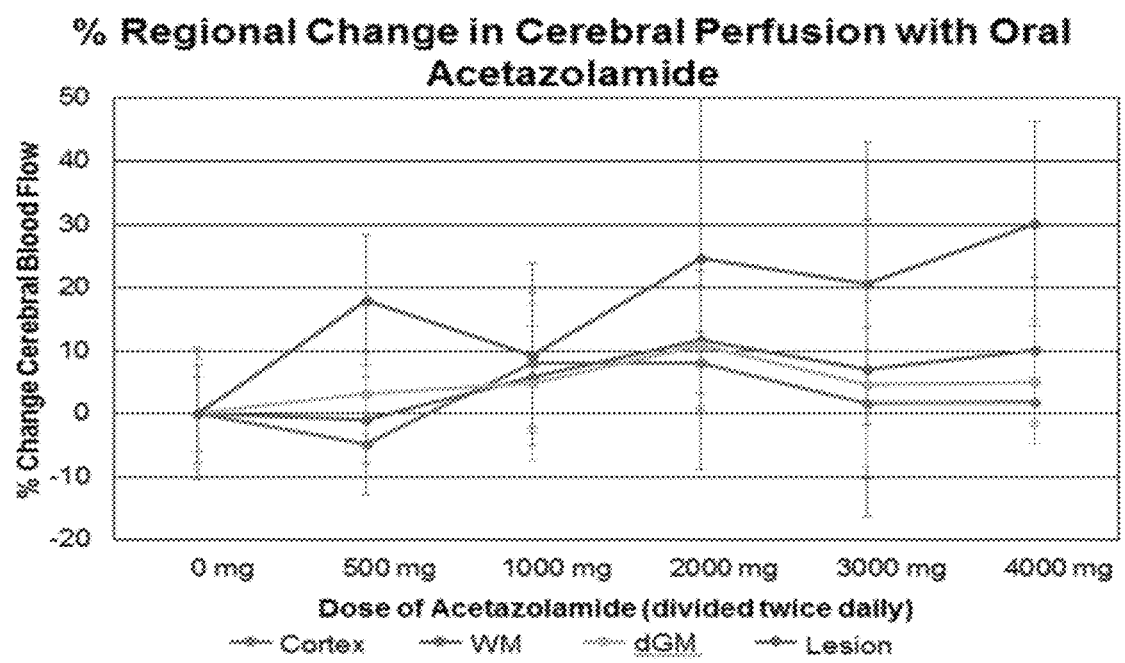
FIG. 5: Percent Change in Regional CBF with Oral ACZ. Five MS patients were treated with twice daily oral ACZ tablets. Patients continued on the indicated twice daily dose of ACZ for two weeks and were assessed using pCASL MRI prior to each time point. Specific pCASL images were retaken at the start and end of the imaging session to determine reproducibility.
Figure 6:
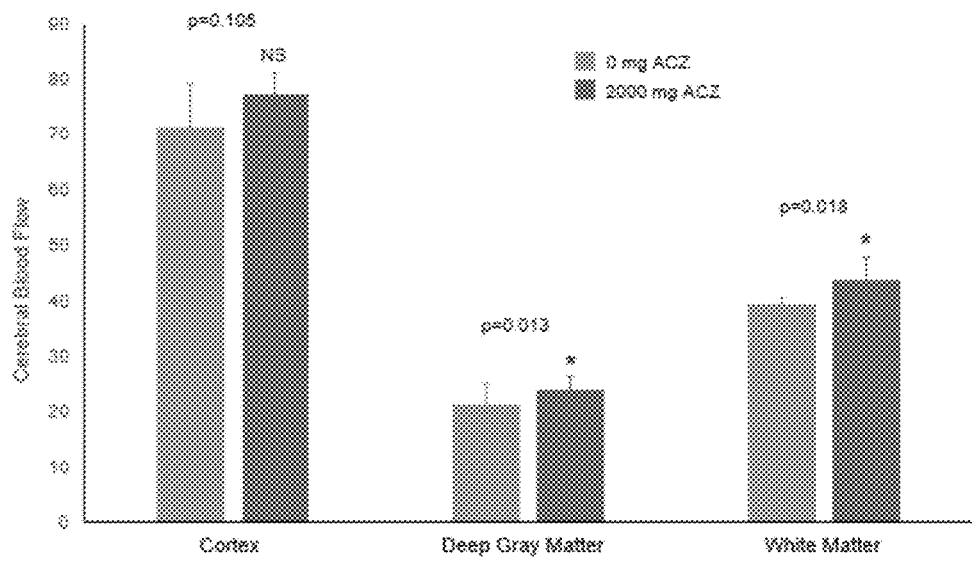
FIG. 6: Mean Change in Regional Cerebral Perfusion with Oral Acetazolamide. Mean change is shown for patients from the test in FIG. 5.

It was suspected that a sustained change in CBF would be necessary to impact lesion evolution and potentially clinical disability. Oral ACZ may prove a practical and effective chronic adjunct therapy for patients with MS. Therefore, a dose-escalation study was done to quantify the degree to which oral ACZ in divided daily doses increases CBF. Patients with stable MS were treated with escalating doses of ACZ from 250 mg twice daily to 2000 mg twice daily. It was shown that sustained increases of 10-25% in global CBF could be obtained at 1000 mg twice daily (FIG. 5). Mean change is global CBF compared to untreated is shown in FIG. 6. Additionally, even at 1000 mg twice daily oral ACZ was well tolerated, with minimal reported adverse events and limited if any potential for tachyphylaxis.

Based upon previous experience, it was anticipated that there would be global and possibly regional differences in the degree of change in CBF even within similar white matter zones. Therefore, for an individual patient, regardless of treatment arm, to quantify measures of tissue integrity DTI measures were utilized in areas of increased CBF relative to proximate areas without altered CBF. Moreover, the delayed start design allows evaluation of these same regions for the period on placebo allowing for each subject to also serve as their own control.

In a proof-of-concept, prospective, randomized, placebo-controlled, delayed start clinical trial that utilizes adjunct daily oral therapy with ACZ to durably improve cerebral perfusion in MS patients with well-established disease and to determine the degree to which improved perfusion impacts the evolution of lesions.

Subject Eligibility—

Eligible subjects are those with established disease, still able to ambulate at least 25 feet in <35 seconds, and either not on disease modifying therapy or continue treatment with approved platform disease modifying therapy therapy (stable on glatiramer acetate (COPAXONE®) or any of the commercially available interferon products (AVONEX®, REBIF®, BETASERON®, EXTAVIA®).

Patients with known hypersensitivity to sulfonamides or derivatives, history of renal, hepatic or cardiovascular disease including congestive heart failure, unstable angina or myocardial infarction, cerebrovascular disease including transient ischemic attack or stroke, history of pulmonary obstruction or emphysema will be excluded from the proposed study.

Study Design—

Forty patients with MS without evidence of clinical relapse in the year prior to study entry will be randomized to receive either ACZ at a dose previously identified or placebo. Half of the eligible patients will be randomly assigned to get ACZ treatment in the first treatment period. The first treatment period consists of a 2-week ramp-up then 24 weeks on ACZ, and then maintained on ACZ for the second treatment period (48-weeks on ACZ overall). The other half would be randomly assigned to placebo for the first 24 weeks and then start on ACZ for the second 24 weeks (the delayed start cohort). Since eligible subjects will be clinically stable, frequent use of oral or IV steroids is not expected. While frequent use of oral or IV steroids is not expected, data from subjects treated with steroids will be treated in one of two ways: either a per-protocol exclusion for 30-days or included as part of an intention-to-treat design.

Subjects will be imaged at pre-specified time points during treatment (see FIG. 7) to evaluate the degree of cerebral perfusion change relative to baseline after 24-week, and 48-week, use of oral ACZ and determine the impact of therapy on the evolution of lesions, normal appearing grey and white matter tissue integrity, and clinical measures of disability. It is anticipated that for a given patient, treatment with ACZ will enhance global CBF at 24 weeks compared with pre-treatment baseline values and the placebo treated cohort, and this will be demonstrated by assessing cerebral perfusion using dynamic susceptibility contrast (DSC)-MRI and pseudo-continuous arterial spin labeling (pCASL), and by measuring tissue integrity within lesions by diffusion tensor imaging (DTI) and diffusion MRI (dMRI). We will also learn if the effect is reproduced in the placebo first cohort following delayed start to ACZ, and/or if benefit requires more than 24 weeks of active therapy or improves further over more than 24 weeks of therapy.

Cerebral Perfusion—

There are several well-established MRI-based techniques to quantify cerebral perfusion. Dynamic susceptibility contrast (DSC), a method using exogenous contrast agent, can accurately and reproducibly quantify CBF, cerebral blood volume (CBV) and mean transit time (MTT) of blood. Contrast-dependent techniques, while robust, necessitate the use of gadolinium chelates, IV compounds that are generally safe to administer with only very rare associated adverse events. Arterial spin labeling (ASL) is a non-invasive MRI technique where spins are tagged using a radio-frequency pulse to determine CBF without the need to administer contrast agent. Pseudo-continuous ASL (pCASL) is a more recent technique that largely overcomes disadvantages of other ASL techniques and has been recently optimized to accurately and reproducibly quantify CBF. DSC is generally considered more reliable when measuring CBF in the deep white matter and provides information about blood volumes and rate of flow that might prove important in understanding vascular pathology and the effects of ACZ. To investigate a causal relationship between changes in global and regional cerebral perfusion and longitudinal changes in tissue integrity, measurements of perfusion will be made at six week intervals. To accomplish this, cerebral perfusion will be evaluated using two robust techniques, pCASL and DSC. CBF measurements using both techniques are strongly correlated, especially for cortical tissues. Combining these perfusion techniques provides independent verification and improved accuracy.

MRI Data Acquisition—

To limit patient discomfort, the scan time of the MRI study is kept under 90 minutes. The standard MRI protocol includes whole brain high resolution sequences acquired in the sagittal plane including 3D T1-weighted magnetization prepared rapid acquisition of gradient echoes (MPRAGE) used for registration, 3D MP2RAGE used for T1 relaxometry, 3D fluid-attenuated inversion recovery (FLAIR), 3D double inversion recovery (DIR) and multi-echo 3D gradient and spin echo (GRASE). In addition to standard sequences, specialized perfusion and diffusion sequences will also be obtained.

Image Processing—

Surface reconstruction and volumetric segmentation will be obtained from the 3DMPRAGE volumes with the FreeSurfer v5.3.0 image analysis suite. 3D-FLAIR images are registered to 3DMPRAGE images and hyperintense lesions manually segmented using Jim v7.0 (Xinapse Systems Ltd, Essex, UK) by an expert technician with >10 years' experience in identifying and segmenting images from patients with MS.

Dynamic Susceptibility Contrast (DSC)-MRI—

DSC-MRI is performed in the transverse plane using a gradient-echo echo planar imaging (EPI) sequence with the following parameters: TR/TE/flip angle: 1750/30/75°, field of view: 224×224 mm; slice thickness: 4 mm; matrix: 128×128; in-plane voxel size: 1.75×1.75 mm. Imaging is performed during the first pass of 0.1 mmol/kg bolus of gadoterate meglumine (DOTAREM®, Guerbet USA, Bloomington, Ind.), infused at 5 ml/sec using an MR-compatible power injector through an 18-gauge IV catheter placed in the antecubital fossa. A series of 60 DSC-MRI images are acquired at 1.75 sec intervals during the first pass of contrast agent. The injection was performed at the 10th acquisition and immediately followed by a bolus injection of saline at the same injection rate. DSC data are analyzed using tools in the FMRIB Software Library (FSL v5.0.7, (see, fsl.fmrib.ox.ac.uk/fsl) and FreeSurfer v5.3.0 (see, surfer.nmr.mgh.harvard.edu). Images are first motion corrected using intramodal brain registration. Voxel-wise quantification of CBF in mL/100 g/min, cerebral blood volume and MTT are obtained using the Vascular Model Based Perfusion Quantification for DSC-MRI (VERBENA) FSL tool. (Chappell et al., 2014).

Pseudo-Continuous Arterial Spin Labeling— pCASL is obtained with a single shot gradient echo EPI sequence with the following parameters: TR/TE of 4300 ms/16 ms and voxel dimension of 3 mm×3 mm×5 mm, number of dynamics of 70, label duration of 1900 ms, post label delay of 2000 ms. pCASL data are analyzed using tools in the FMRIB Software Library and FreeSurfer v5.3.0. After motion correction, tagged and non-tagged images are separated and pair-wise difference images calculated. The Bayesian Inference for Arterial Spin Labeling MRI (BASIL) tool, part of the FMRIB Software Library, is used for voxel-wise quantification of absolute CBF in mL/100 g/min from the difference images using a kinetic model-based approach (as described in Adhya et al., 2006). Partial volume estimates, transformed to pCASL data space, are used to discard voxels found in both GM and WM, and reduce partial volume contamination. CBF maps will be registered to 3DMPRAGE images using a boundary-based registration toolkit available in FreeSurfer.

Measuring Tissue Integrity within Lesions—

Molecular diffusion can vary based upon the properties of the medium. Therefore measures of diffusion within tissues provides information about its microstructural integrity. Pathologic processes that alter tissue organization affect permeability resulting in abnormal water diffusivity. In medium without oriented microstructure, diffusivity occurs in three dimensions. White matter fiber tracts consist of aligned myelinated axons and molecular diffusivity is greater parallel to the fiber tract direction. Diffusion tensor imaging (DTI) is a reliable, validated technique that quantitatively measures molecular diffusivity within tissue.

Numerous studies have shown increased mean diffusivity (MD) values in lesions of MS patients when compared with normal white matter or healthy controls. MD is a measure of the average molecular motion independent of tissue directionality, and is affected by cellular size and integrity. Larger values of MD correlate with reduced cellularity and more free space within tissues. Fractional anisotropy (FA) is one of the most commonly used measures of deviation from isotropy, equal diffusion of water in the three measured directions, and reflects the degree of alignment of cellular structures within fiber tracts as well as their structural integrity. FA values decrease within MS lesions when compared to normal white matter. The directional diffusivities describe water movement radial diffusivity (RD) ($\lambda 1$) and longitudinal axial diffusivity (AD) ($\lambda 2$) in compact white matter tracts. It has been previously shown that decreased AD is associated with axonal injury and increased RD associated with myelin injury. It is anticipated that for a given patient, MD will decrease and FA increase in lesioned tissue within areas with improved CBF, relative to areas without change in CBF, for the period while on ACZ treatment.

MD within the MS lesion and various white matter regions in patients on oral ACZ have been determined (FIG. 8). To quantify change in tissue integrity, using quantitative DTI, within areas of increased cerebral blood flow (CBF) relative to proximate areas without altered CBF. It is anticipated that MD will decrease and FA increase in areas with improved CBF for the period while on ACZ treatment, and that these changes might be larger within the lesion rim. It is further anticipated that these techniques will allow characterization of the durability of the effect of ACZ on perfusion and the temporal relationship between change in perfusion and measures of microstructural integrity. It is hypothesized that MD and FA change within either the lesion as a whole, or predominantly in the rim during therapy with ACZ.

Diffusion MRI (dMRI) Methods—

Diffusion-weighted imaging (DWI) data will be acquired using a single-shot spin-echo diffusion-sensitized echo-planar imaging sequence with balanced alternating polarity Icosa21 tensor encoding scheme at different b-factors=500, 1500 & 2500 s/mm$^2$, TR/TE=12000/75 ms; isotropic voxel=2 mm. This multi-shell dMRI protocol is designed to provide multiple intrascan estimates of diffusivity and anisotropy to estimate signal-to-noise ratio and b-factor dependence of the estimated metrics. The multiple b-factor design will also allow modeling of free water in the extracellular space. In addition, the same data can be used to obtain non-Gaussian measures such as diffusion kurtosis imaging (DKI) and neurite (axons and dendrites) orientation and dispersion (NODDI).

DTI Data Analysis—

Multi-shell DWI data will be registered to the b0 images (without any diffusion weighting) to correct for eddy current-induced geometric distortions using affine transformation with twelve degrees of freedom. DWI data will be prepared to undergo different analysis and extensive modeling computational pipelines that include single tensor DTI and atlas-based analyses and fiber tractography. The three eigenvalues, $\lambda 1$, $\lambda 2$, and $\lambda 3$ and calculated values for MD, RD, AD and FA are obtained using the FDT software from the FSL toolbox.

As can be seen in FIG. 8, CBF increased in the region with the larger T2 to T1 mismatch (panel g compared with panel d). As would be expected after only 2 weeks at target dose, qualitative DTI and T2 relaxometry measures changed little. These changes were seen with good reproducibility.

Measuring Changes in Cerebral Atrophy after ACZ—

In addition to measures of MD and FA, measurement of cerebral atrophy following ACZ administration is a key secondary endpoint. Global and regional cerebral atrophy has been correlated with worsening disability in MS patients and regional volume loss may be a more sensitive marker of degeneration. In addition to changes within lesional tissue, this study will evaluate whether improving cerebral perfusion with ACZ will reduce regional cortical atrophy measured using several complementary techniques as described. It is anticipated that for a given patient, treatment with ACZ will result in significant differences in composite scores for evaluated clinical disability measures at 24-weeks and/or 48-weeks on ACZ therapy, compared to with pre-treatment baseline values. These measures will be assessed by composite change and using the expanded disability status score (EDSS), the 9-hole peg test (9hpt) for either the dominant or non-dominant hand, timed 25-foot walk (T25FW), or improved accuracy for symbol digit modalities test (SDMT).

Figure 7:
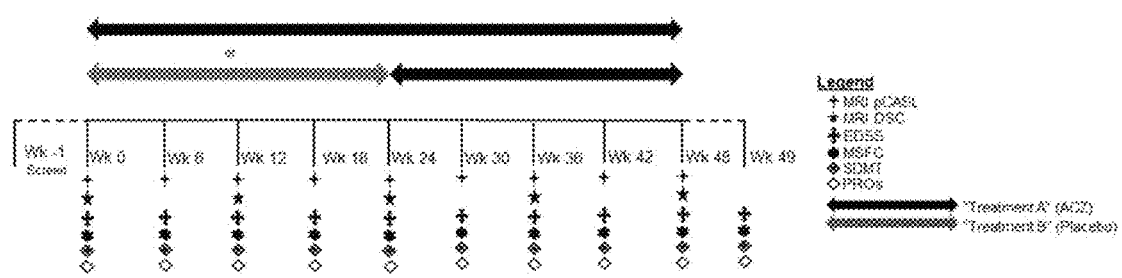
FIG. 7: Oral ACZ Study Design. Forty MS patients without evidence of clinical relapse in the year prior to study entry and who are stable on approved platform disease modifying therapies or untreated will be enrolled. Half of the patients will be randomly assigned to get twice daily oral ACZ for 48 weeks with the other half assigned to placebo for the first 24 weeks and then switched to twice daily oral ACZ for another 24 weeks. At pre-specified time points, patients will receive conventional MRI as well as specialized sequences to assess cerebral hemodynamics, DTI, relaxometry and myelin-water fraction. At each of these time points, patients will also be evaluated by a blinded rater to determine MSFC and EDSS as well as complete various patient-reported quality of life assessments.

Improving cerebral perfusion might reduce the mismatch between energy demand and production, thereby decreasing virtual hypoxia and resultant axonal degeneration. If reduced blood flow is an important contributor of irreversible neurologic disability, then improved perfusion would be expected to reduce clinical disability progression. This study will determine if clinical disability, measured by two Multiple Sclerosis Functional Composite scale (MSFC) domains, 9HPT and T25FW, is different after 24 weeks on ACZ therapy relative to baseline. As seen in FIG. 7, subjects will be evaluated by a clinical rater prior to start of therapy and every six weeks for a total of 24 weeks on ACZ and placebo. MSFC domains were chosen because of the speed of evaluation and good interrater reliability.

Expanded Disability Status Score (EDSS)—

The EDSS is a clinician-administered assessment scale used to describe disease progression in patients with MS, and is widely used as a primary outcome measure in large randomized clinical trials. The EDSS is an ordinal rating system with values ranging from 0 (normal neurological status) to 10 (death due to MS). After EDSS 1, scores increase in 0.5 increment intervals. One short-coming of the EDSS is the focus on walking capacity. Mid-range scores (EDSS 4-6) are dependent on walking ability while upper range scores (EDSS>6) primarily measure the degree to which assistance devices are necessary.

Multiple Sclerosis Functional Composite Scale (MSFC)—

The MSFC combines quantitative measures of upper extremity, lower extremity, and cognitive function into a single composite that has been validated in several large multi-center clinical trials as a robust metric to predict disability outcomes but as a z-score lacks ready translation for the clinician or acceptance as an outcome measure by the FDA.

9-Hole Peg Test (9HPT)—

The 9HPT measures upper extremity function based upon the time needed for the patient to insert and remove nine pegs from a board. Both dominant and non-dominant hands are tested, and the score reflects the average time for both hands. It is generally accepted that the SHPT is more sensitive than the EDSS in detecting deteriorations in upper extremity function, with >20% worsening a better predictor of overall clinical disability progression.

Timed 25 Foot Walk (T25FW)—

The T25FW assesses change in lower extremity function. Unlike the EDSS, which requires a rater with knowledge of the neurological exam, the T25FW is a simple test that measures the time required for a patient to safely ambulate 25 feet without rest. Benefits include good inter-rater reliability and ability to measure change in lower extremity function, even for a patient requiring an assistance device. Generally, a time increase of 20% or greater indicates a clinically meaningful impairment in gait.

Symbol Digit Modalities Test (SDMT)—

The SDMT can be used to evaluate divided attention though additional parameters are tested including visual scanning, tracking and motor speed. Using a reference key, participants have ninety seconds to pair specific numbers with geometric figures. Since participants can give either written or spoken responses, the test can be used with subjects having motor or speech disorders. In addition, because it involves only geometric figures and numbers, the SDMT is relatively culture free and can be given to non-English speaking subjects. Test-retest reliability has been shown to be 0.80 for the written and 0.76 for the oral version in normal healthy adults. SDMT is a measure of cognitive processing speed sensitive to the detection of cognitive impairment in MS and has been previously shown to be associated with brain MRI metrics and functional disability and has excellent validity as a measure of cognition in MS. SDMT will be assessed at each study visit.

Patient-Reported Outcome (PRO)—

It is anticipated that for a given patient, treatment with ACZ will result in significant differences in the patient-reported outcome (PRO) measures for Modified Fatigue Impact Scale (MFIS) and Twelve Item MS Walking Scale (MSWS-12) at 24-weeks and/or 48-weeks on ACZ therapy compared to with pre-treatment baseline values. PROs may offer complementary information when assessing disability, as scores reliant solely upon clinician raters fail to adequately weight fatigue or mental health problems. In the absence of including PROs, any effect of treatment not directly related to physical disability might go unnoticed. Change in PRO disability measures, either improvement or worsening, will be correlated with CBF, CBV and MTT using the Spearman rank correlation from baseline to end of ACZ treatment.

MFIS & MSWS-12—

The MFIS is a modified version of the 40-item Fatigue Impact Scale (FIS) originally developed to assess the effects of fatigue on quality of life in patients with MS. The MFIS is a multidimensional, 21-item questionnaire detailing subjective information related to fatigue within nine physical, ten cognitive, and two psychosocial domains over a 4-week period. Participants rate each item using a 5-point Likert-type scale ranging from never, scored as "0", to always, scored as "4", with higher scores indicating a greater impact of fatigue on quality of life. There is good validity and reliability of the MFIS over 6 months with a change in score of >10 considered clinically relevant. The MSWS-12 is a previously validated self-rated measure of walking quality. It contains 12 questions scored on a 1 to 5 Likert-type scale with a recall period of two weeks. The MSWS-12 can assess walking impairment across a larger range of disability with higher scores indicating greater perceived walking difficulty.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adhya et al., *NeuroImage*, 33:1029-35, 2006.
Chappell et al., *Magn. Reson. Med.*, doi: 10.1002/mrm.25390, 2014.
Dodgson et al. *J Appl Physiol*, 68:2443-2450, 1990.
Filippi, M., et al. *Neurology* 56(3): 304-311, 2001.
Narayana, P. A., et al. *Mult Scler* 20(3): 365-373, 2014.
Papadaki, E. Z., et al. *Eur J Neurol* 21(3): 499-505, 2014.
Papadaki, E. Z., et al. *Magn Reson Med* 68(6): 1932-1942, 2012.
Polman, C. H., et al. *Ann Neurol* 69(2): 292-302, 2011.
Trapp, B. D. and P. K. Stys, *Lancet* Neurol 8(3): 280-291, 2009.
U.S. Pat. Nos. 4,383,098, 4,416,890, 4,426388, 4,677,115, 4,797,413, 4,820,848, 4,824,968, 4,863,922, 5,157,044, and 5,225424
Wuerfel, J., et al. *Brain* 127(Pt 1): 111-119, 2004.

What is claimed is:

1. A method of treating a brain lesion in a subject diagnosed with multiple sclerosis (MS) comprising orally administering a carbonic anhydrase inhibitor to the subject in an effective amount to increase cerebral perfusion.

2. The method of claim 1, wherein the carbonic anhydrase inhibitor is acetazolamide (ACZ), dichlorphenamide, methazolamide, dorzolamide, or brinzolamide.

3. The method of claim 2, wherein the carbonic anhydrase inhibitor is acetazolamide (ACZ).

4. The method of claim 1, wherein the MS is relapsing-remitting, secondary progressive, or primary progressive MS.

5. The method of claim 1, wherein the brain lesion is further defined as a subacute or chronic brain lesion.

6. The method of claim 1, wherein the brain lesion is a T1 hypointense lesion.

7. The method of claim 1, wherein the brain lesion is caused by cerebral hypoperfusion.

8. The method of claim 1, wherein administering is for at least 2 months, 6 months, or 12 months.

9. The method of claim 1, wherein between 1000 and 4000 mg of carbonic anhydrase inhibitor is administered daily.

10. The method of claim 1, wherein the carbonic anhydrase inhibitor is formulated for immediate release.

11. The method of claim 1, wherein the carbonic anhydrase inhibitor is formulated for sustained release.

12. The method of claim 1, further comprising at least a second therapeutic.

13. The method of claim 12, wherein the second therapeutic is a MS therapy.

14. The method of claim 13, wherein the MS therapy is glatiramer acetate, interferon beta-1β, and/or interferon-1α.

15. The method of claim 13, wherein the MS therapy is a bone marrow or stem cell transplant.

16. The method of claim 12, wherein the second therapeutic is anti-inflammatory.

17. A pharmaceutical composition comprising between 1000 and 4000 mg of acetazolamide per dose, wherein the pharmaceutical composition is formulated for oral administration.

18. A method of treating brain lesion in a subject comprising orally administering an effective amount of a composition according to claim 17 to a subject.

* * * * *